US00PP20920P2

(12) United States Plant Patent
Ranney

(10) Patent No.: US PP20,920 P2
(45) Date of Patent: Apr. 6, 2010

(54) FLOWERING QUINCE PLANT NAMED 'PINK STORM'

(50) Latin Name: *Chaenomeles speciosa*
Varietal Denomination: Pink Storm

(75) Inventor: Thomas G. Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 12/381,215

(22) Filed: Mar. 9, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para
(74) *Attorney, Agent, or Firm*—Jondle & Associates, P.C.

(57) ABSTRACT

'Pink Storm' is a new quince plant particularly distinguished by a medium-sized, upright, multi-stemmed shrub with occasional parthenocapic fruit formation, large, double-flowers with pink petals, and thornless stems, is disclosed.

2 Drawing Sheets

Genus and species: *Chaenomeles speciosa.*

Variety denomination: 'Pink Storm'.

BACKGROUND OF THE INVENTION

The present invention comprises a new and distinct cultivar of flowering quince, botanically known as *Chaenomeles speciosa,* and hereinafter referred to by the cultivar name 'Pink Storm'. This new flowering quince was developed through a breeding program at North Carolina State University, Mills River, N.C. 'Pink Storm' is an $F_1$ hybrid between the female parent, *Chaenomeles speciosa* 'Spitfire' (unpatented) and the male parent, *Chaenomeles speciosa* 'Dragons Blood' (unpatented). The first asexual propagation of 'Pink Storm' was carried out in June 2003 by rooting stem cuttings at the North Carolina State University, Mountain Horticultural Crops Research Station, Mills River, N.C. and has been asexually reproduced repeatedly by vegetative cuttings in North Carolina over a five year period.

'Pink Storm' roots readily from softwood cuttings treated with a basal dip of 5,000 ppm indole butyric acid (potassium salt) in water. 'Pink Storm' has been found to retain its distinctive characteristics through successive asexual propagations.

Plant Breeder's Rights for this cultivar have not been applied for. 'Pink Storm' has not been made publicly available more than one year prior to the filing date of this application.

SUMMARY OF THE INVENTION

The following are the most outstanding and distinguishing characteristics of this new cultivar when grown under normal horticultural practices at North Carolina State University, Mountain Horticultural Crops Research Station, Mills River, N.C.

1. A medium-sized, upright, multi-stemmed shrub with occasional parthenocapic fruit formation;
2. Large, double-flowers with pink petals; and 3. Thornless stems.

DESCRIPTION OF THE PHOTOGRAPHS

This new quince plant is illustrated by the accompanying photographs which show the plant's form, foliage and inflorescences. The colors shown are as true as can be reasonably obtained by conventional photographic procedures. The photographs were taken on Apr. 10, 2008 on 2-year-old plants, growing under greenhouse conditions in Mills River, N.C.

DESCRIPTION OF THE NEW CULTIVAR

Figure 1:
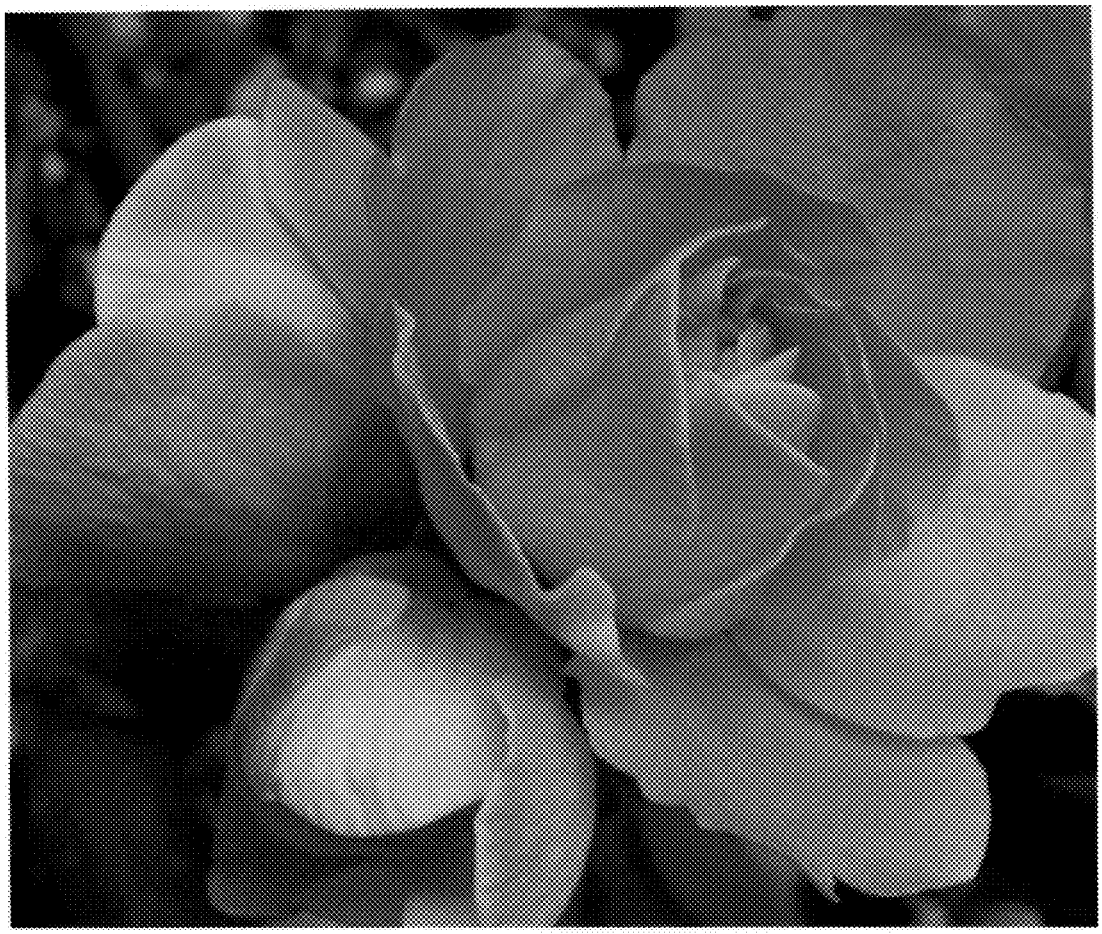
FIG. 1 shows the large, pink, double flower, prior to anthesis.
Figure 2:
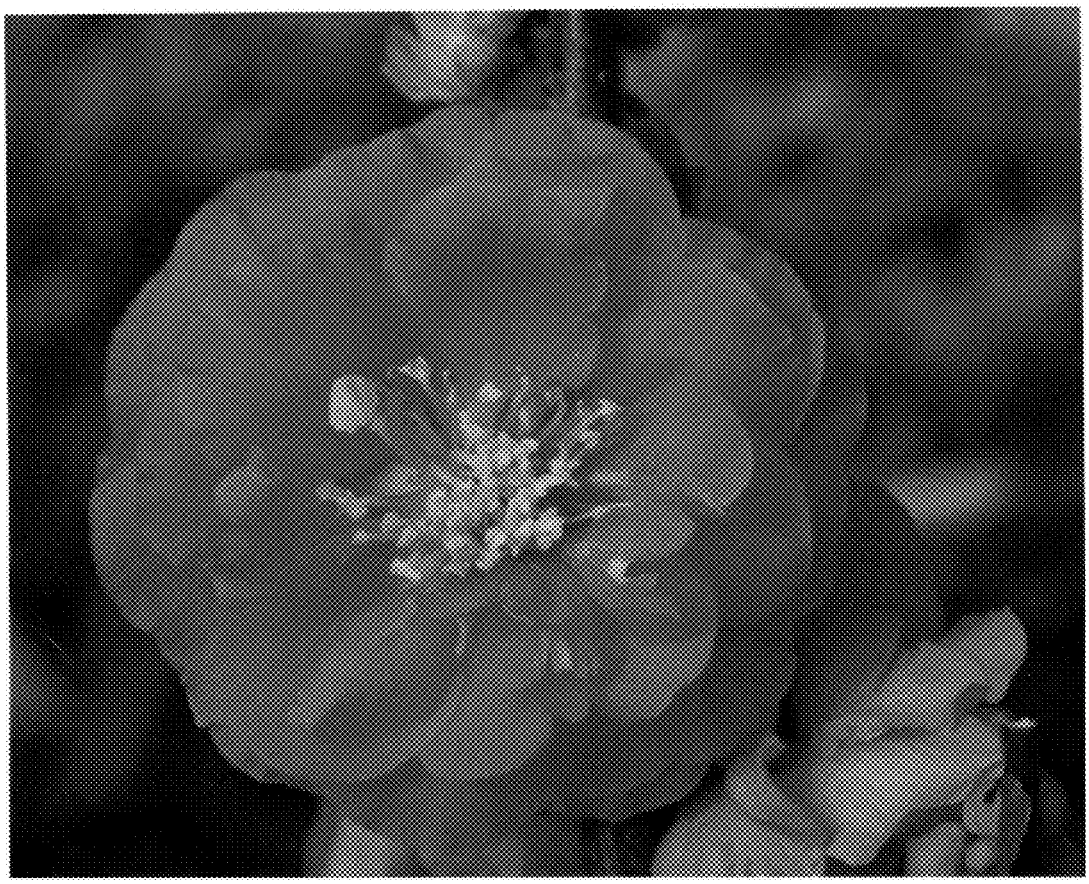
FIG. 2 shows the fully open flower at anthesis.

The following detailed description sets forth the distinctive characteristics of 'Pink Storm'. The detailed description was taken on 7-year-old plants growing under landscape conditions in Mills River, N.C. in April 2008. Color references are to The R.H.S. Colour Chart of The Royal Horticultural Society of London (R.H.S.), 2001 Edition.

DETAILED BOTANICAL DESCRIPTION

Classification:
- *Botanical name.*—*Chaenomeles speciosa.*
- *Common name.*—Quince.

Parentage:
- *Female parent.*—*Chaenomeles speciosa* 'Spitfire' (unpatented).
- *Male parent.*—*Chaenomeles speciosa* 'Dragons Blood' (unpatented).

Plant description:
- *Growth habit.*—Upright.
- *Plant shape.*—Fusoid.
- *Height at maturity.*—2 meters to 3.33 meters.
- *Width at maturity.*—2 meters to 2.67 meters.

Stem:
- *Mature stem color.*—RHS N199B (Grey-brown).
- *Immature stem color.*—RHS 144C (Yellow-green).
- *Quantity of thorns.*—Thorns are absent.

Leaves:

*Type.*—Deciduous.

*Arrangement.*—Alternate.

*Shape.*—Elliptic.

*Apex.*—Acute.

*Base.*—Attenuate.

*Margin.*—Serrulate.

*Surface texture (both surfaces).*—Glabrous (not pubescent) to lustrous (shiny).

*Mature leaf size.*—Length: Average is 6.55 cm (range is 5.11 cm to 7.96 cm). Width: Average is 3.87 cm (range is 3.27 cm to 4.64 cm).

*Immature leaf color.*—Adaxial (upper) surface: Flushes RHS N34 (Orange-red), which changes to RHS 147A (Yellow-green). Abaxial (lower) surface: Flushes RHS 53A (Red), which changes to RHS 147B (Yellow-green).

*Mature leaf color.*—Adaxial (upper) surface: RHS 147A (Yellow-green). Abaxial (lower) surface: RHS 148B (Yellow-green).

*Stipule.*—Color: Adaxial (upper) surface: RHS 147A (Yellow-green). Abaxial (lower) surface: RHS 148B (Yellow-green). Size: Immature: Length: Average is 0.97 cm (range is 0.88 cm to 1.08 cm). Width: Average is 1.3 cm (range is 1.25 cm to 1.35 cm). Mature: Length: Average is 1.43 cm (range is 1.18 cm to 1.7 cm). Width: Average is 2.28 cm (range is 2.04 cm to 2.41 cm).

*Leaf attachment.*—Petiolate.

*Petiole.*—Shape: Laterally compressed to sulcate. Length: Average is 0.35 cm (range is 0.28 cm to 0.44 cm). Width: Average is 0.096 cm (range is 0.082 cm to 0.12 cm). Surface: Glabrous (not pubescent).

Flower:

*Number of flowers per cluster.*—2 to 5.

*Type.*—Double flower.

*Habit.*—Seasonal (spring).

*Flowering season.*—Early spring through late spring.

*Lastingness of flower on the plant.*—7 to 21 days.

*Fragrance.*—Absent.

*Length at anthesis.*—Average is 5.2 cm (range is 4.4 cm to 6.0 cm).

*Self cleaning or persistent.*—Self-cleaning.

*Petal.*—Number of petals per flower: Average is 34 (range is 29 to 40) Color, adaxial (upper) surface at anthesis: As the flower begins to open, the petals are RHS 50C to RHS 50D (Pink); at anthesis, the petals are RHS 47C to RHS 47D (Pink) with occasional RHS 69D (light Red-purple) streaks on the interior most petals and petaloid anthers. Color, abaxial (lower) surface at anthesis: As the flower begins to open, the petals are RHS 50C to RHS 51D (Pink); at anthesis, the petals are RHS 47B to RHS 47C (Pink) with occasional RHS 69D (light Red-purple) streaks on the interior most petals and petaloid anthers. Basal color: As the flower begins to open, petals are RHS 144D (Yellow-green) and at anthesis become closest to RHS 56B (Pink). Surface texture (both surfaces) and appearance: Soft, thin and glabrous (not pubescent). Shape: Flabellate. Apex: Rounded. Base: Cuneate. Margin: Semi-crenate to entire. Length: Average is 2.12 cm (range is 0.75 cm to 3.07 cm). Width: Average is 1.74 cm (range is 0.84 cm to 2.5 cm). Petals, fused or unfused: Unfused.

*Peduncle.*—Shape: Cylindrical. Length: Average is 0.44 cm (range is 0.33 cm to 0.54 cm). Width: Average is 0.13 cm (range is 0.10 cm to 0.15 cm). Color: Closest to RHS 144A (Yellow-green). Surface texture: Glabrous (not pubescent).

Calyx/receptacle:

*Shape and arrangement.*—5-lobed and globular to globular conical.

*Calyx/receptacle size.*—Length: Average is 1.62 cm (range is 1.44 cm to 1.9 cm). Width: Average is 1.55 cm (range is 1.47 cm to 1.6 cm). Depth: Average is 0.53 cm (range is 0.50 cm to 0.56 cm).

*Lobe number.*—5.

*Lobe apex.*—Closest to retuse.

*Lobe base.*—Fused.

*Lobe margin.*—Ciliate.

*Lobe length.*—Average is 0.40 cm (range is 0.3 cm to 0.5 cm).

*Lobe width.*—Average is 0.575 cm (range is 0.5 cm to 0.65 cm).

*Lobe color, adaxial (upper) surfaces.*—The base color is initially RHS 141A (Green) and matures to RHS 187B (Greyed-purple) with RHS 42A (Red) margins.

*Lobe color, abaxial (lower) surfaces.*—RHS 138A (Green).

*Lobe surface texture, adaxial (upper) surface.*—Glabrous (not pubescent).

*Lobe surface texture, abaxial (lower) surface.*—Pubescent.

Reproductive organs:

*Stamen.*—Quantity per flower: About 76. Shape: Filament. Color: Translucent RHS 142D (Green), RHS 48A (Red) in senescence. Attachment: Dorsifixed. Length: Average is 0.6 cm (range is 0.6 cm to 1.2 cm). Width: Less than 0.05 cm. Anther: Length: Average is 0.20 cm (range is 0.1 cm to 0.275 cm). Width: Average is 0.125 cm (range is 0.1 cm to 0.15 cm). Shape: Ovoid. Color: RHS 12C (Yellow). Pollen color: RHS 12C (Yellow). Pollen amount: Very sparse.

*Pistil.*—Absent.

*Ovary.*—Absent.

Fruit/seed set:

*General.*—Fruit is generally lacking, occasional parthenocarpic fruit formation.

*Fruit shape.*—Furrowed oblate.

*Fruit surface texture.*—Glabrous.

*Fruit color.*—RHS 138B (Green) with RHS 142D (Green) speckling.

*Quantity of seed.*—None.

Disease and insect resistance: No significant disease or insect pests have been observed.

COMPARISON WITH PARENTAL LINES AND KNOWN CULTIVARS

'Pink Storm' is distinguished from the female parent, *Chaenomeles speciosa* 'Spitfire' (unpatented) in that the flower color of 'Pink Storm' is pink, while the flowers of 'Spitfire' are red.

'Pink Storm' is distinguished from the male parent, *Chaenomeles speciosa* 'Dragons Blood' (unpatented) in that the flower color of 'Pink Storm' is pink, while the flowers of 'Dragons Blood' are red.

Table 1 shows the differences between 'Pink Storm' and commercial varieties 'Jet Trail' (unpatented) and 'Toyo-Nishiki' (unpatented).

TABLE 1

COMPARSION TO COMMERCIAL CULTIVARS

| | Cultivar | | |
|---|---|---|---|
| Trait | 'Pink Storm' | 'Jet Trail' | 'Toyo-Nishiki' |
| Flower Color | Pink, RHS 47B to RHS 50D | White, RHS N155 | Emerges White, RHS N155; Fading to Pink, RHS 49A to RHS 51C |
| Petal Number/Flower | 29 to 40 | 5 to 6 | 5 |
| Flower Diameter | 4.4 cm to 6.0 cm | 5.0 cm to 6.0 cm | 3.0 cm to 5.6 cm |

TABLE 1-continued

COMPARSION TO COMMERCIAL CULTIVARS

| | Cultivar | | |
|---|---|---|---|
| Trait | 'Pink Storm' | 'Jet Trail' | 'Toyo-Nishiki' |
| Pistil | Lacking | Present | Generally Present |
| Fruit | Lacking | Present | Present |
| Thorns | Lacking | Lacking | Present |

I claim:

1. A new and distinct cultivar of quince plant as shown and described herein.

* * * * *